United States Patent
Dethloff et al.

(10) Patent No.: US 12,024,548 B2
(45) Date of Patent: Jul. 2, 2024

(54) RAPID METHOD FOR CLONING AND EXPRESSION OF COGNATE ANTIBODY VARIABLE GENE SEGMENTS

(71) Applicant: Hoffmann-La Roche Inc., Little Falls, NJ (US)

(72) Inventors: Simone Dethloff, Bichl (DE); Erhard Kopetzki, Penzberg (DE); Dominique Ostler, Aidling (DE); Stefan Seeber, Sindelsdorf (DE); Georg Tiefenthaler, Sindelsdorf (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/244,909

(22) Filed: Jan. 10, 2019

(65) Prior Publication Data
US 2019/0382469 A1    Dec. 19, 2019

Related U.S. Application Data

(63) Continuation of application No. 15/480,533, filed on Apr. 6, 2017, now abandoned, which is a continuation of application No. 14/310,966, filed on Jun. 20, 2014, now abandoned, which is a continuation of application No. PCT/EP2012/076155, filed on Dec. 19, 2012.

(30) Foreign Application Priority Data

Dec. 21, 2011   (EP) ..................................... 11194861

(51) Int. Cl.
| | | |
|---|---|---|
| C12N 15/85 | (2006.01) | |
| C07K 16/00 | (2006.01) | |
| C12N 5/0781 | (2010.01) | |
| C12N 15/10 | (2006.01) | |
| C12P 21/02 | (2006.01) | |

(52) U.S. Cl.
CPC ............ C07K 16/00 (2013.01); C12N 5/0635 (2013.01); C12N 15/1086 (2013.01); C12N 15/85 (2013.01); C12P 21/02 (2013.01); C07K 2317/14 (2013.01); C07K 2317/56 (2013.01); C12N 2510/02 (2013.01)

(58) Field of Classification Search
None
See application file for complete search history.

(56) References Cited

U.S. PATENT DOCUMENTS

| | | |
|---|---|---|
| 2006/0051348 A1 | 3/2006 | Gorlach |
| 2007/0269868 A1 | 11/2007 | Jensen et al. |
| 2011/0223176 A1 | 9/2011 | Barlow et al. |

FOREIGN PATENT DOCUMENTS

| | | |
|---|---|---|
| WO | 00/05268 | 2/2000 |
| WO | 2007/031550 A2 | 3/2007 |
| WO | 2008/045140 A1 | 4/2008 |
| WO | 2008/144763 A2 | 11/2008 |
| WO | 2010/056898 A2 | 5/2010 |
| WO | 2010/142423 A2 | 12/2010 |
| WO | 2011/147903 A1 | 12/2011 |

OTHER PUBLICATIONS

Anonymous: In-Fusion® HD Cloning Kit User Manual, Clontech Laboratories, Inc. a Takara Bio Company XP002678455 URL: http://www.clontech.com/xxcit_ibcGetAttachment.jsp? citemid:17497, pp. 1-15 (2011).
European Search Report for EP Application No. 11194861.8.
PCT International Search Report and Written Opinion for PCT/EP2012/076155.
Haun et al., "Rapid, reliable ligation-independent cloning of PCR products using modified plasmid vectors" Biotechniques 13(4):515-518 (Oct. 1992).
Jin et al., "A rapid and efficient single-cell manipulation method for screening antigen-specific antibody-secreting cells from human peripheral blood" Nature Medicine 15(9):1088-1093 (Sep. 2009).
Jones et al., "A method for rapid, ligation-independent reformatting of recombinant monoclonal antibodies" Journal of Immunological Methods 354:85-90 ( 2010).
Kurosawa et al., "Target-selective homologous recombination cloning for high-throughput generation of monoclonal antibodies from single plasma cells" BMC Biotechnology (http://www.biomedcentral.com/1472-6750/11/39), 11 ( 2011).
Li et al., "Harnessing homologous recombination in vitro to generate recombinant DNA via SLIC" Nature Methods 4(3):251-256 ( 2007).
Lightwood et al., "Antibody generation through B cell panning on antigen followed by in situ culture and direct RT-PCR on cells harvested en masse from antigen-positive wells" Journal of Immunological Methods 316:133-143 ( 2006).
Liu et al., "Research advance on ligation-independent cloning (LIC) method" Genomics and Applied Biology (English abstract), 30 ( 2011).

(Continued)

*Primary Examiner* — Michael D Burkhart
(74) *Attorney, Agent, or Firm* — Baker Botts L.L.P

(57) ABSTRACT

In the method as reported herein the isolation of nucleic acid segments encoding antibody variable domains and the insertion of the isolated nucleic acid segments in eukaryotic expression plasmids is performed without the intermediate isolation and analysis of clonal intermediate plasmids. Thus, in the method as reported herein the intermediate cloning, isolation and analysis of intermediate plasmids is not required, e.g. by analysis of isolated transformed *E. coli* cells.

6 Claims, No Drawings

Specification includes a Sequence Listing.

(56) References Cited

OTHER PUBLICATIONS

Luo et al., "Construction and Expression of a Mouse-human Chimeric Antibody against Hepatitis E Virus" Chinese Journal of Virology (English abstract), 20 ( 2004).

Masri et al., "Cloning and expression in E. coli of a functional Fab fragment obtained from single human lymphocyte against anthrax toxin" Molec Immunol 44:2101-2106 ( 2007).

Thieme et al.,"Quick and Clean Cloning: A Ligation-Independent Cloning Strategy for Selective Cloning of Specific PCR Products from Non-Specific Mixes" PLoS One 6(6):e20556 (Jun. 2011) pp. 1-12.

Tiller et al., "Efficient generation of monoclonal antibodies from single human B cells by single cell RT-PCR and expression vector cloning" J Immunol Methods 329(1-2):112-124 (Jan. 2008).

Weitkamp et al., "Generation of recombinant human monoclonal antibodies to rotavirus from single antigen-specific B cells selected with fluorescent virus-like particles" J Immunol Meth 275:223-237 ( 2003).

Zubler et al., "Activated B cells express Receptors for, and proliferate in response to, pure interleukin 2" J Exp Med 160:1170-1183 (Oct. 1984).

Zubler, "Polyclonal B cell responses in the presence of defined filler Cells: Complementary effects of lipopolysaccharide and anti-immunoglobulin antibodies" Eur. J. Immunol. 14:357-363 ( 1984).

Farahmand, L. et al., "Ligation Independent Cloning of Polycistronic, Genetically Modified, HuMAb4D5-8 F(ab')2, in Bacterial Plasmid" Avicenna J Med Biotechnol 4(1):15-22 (Jan. 31, 2012).

Grimaitre et al., "Human naive B cells cultured with EL-4 T cells mimic a germinal center-related B cell stage before generating plasma cells. Concordant changes in Bcl-2 protein and messenger RNA levels" Eur. J. Immunol. 27:199-205 ( 1997).

Guo et al. Methods in Molecular Biology "Chapter 12 Cloning PCR Products" Walker, John M., Second edition, Humana Press, vol. 192:111-119 ( 2002).

Li et al. Gene Synthesis: Methods and Protocols, Methods in Molecular Biology "Chapter 5 Slic: A Method for Sequence- and Ligation-Independent Cloning" Jean Peccoud, First edition, Totowa, NJ:Humana Press, vol. 852:51-59 (2012).

Li et al., "Harnessing homologous recombination in vitro to generate recombinant DNA via SLIC" Nature Methods 4(3):251-256 (Mar. 2007).

Liao, H., et al., "Highthroughput isolation of immunoglobulin genes from single human B cells and expression as monoclonal antibodies" J Virol Methods 158(1-2):171-179 (Jun. 1, 2009).

Mander et al. Comprehensive Natural Products II Chemistry and Biology "Chapter 9.19.4.4 Ligation-Independent Cloning" Lew Mander, First edition, Kidlington, UK:Elsevier Ltd, vol. 9:705 ( 2010).

Seeber. S., et al., "A robust high throughput platform to generate functional recombinant monoclonal antibodies using rabbit B cells from peripheral blood" PLOS One 9(2):e86184-14 (Feb. 4, 2014).

Tiller, T., "Single B cell antibody technologies" N Biotechnol 28(5):453-457 (Sep. 1, 2011).

Wen et al., "Limiting dilution assay for human B cells based on their activation by mutant EL4 thymoma cells: total and antimalaria responder B cell frequencies" Eur. J. Immunol. 17:887-892 ( 1987).

RAPID METHOD FOR CLONING AND EXPRESSION OF COGNATE ANTIBODY VARIABLE GENE SEGMENTS

CROSS-REFERENCE TO RELATED APPLICATIONS

This application is a continuation of U.S. patent application Ser. No. 15/480,533, filed Apr. 6, 2017, which is a continuation of U.S. patent application Ser. No. 14/310,966, filed Jun. 20, 2014, which is a continuation of International Patent Application No. PCT/EP2012/076155, having an international filing date of Dec. 19, 2012, the entire contents of which are incorporated herein by reference in its entirety, which claims benefit under 35 U.S.C. § 119 to European Patent Application No. 11194861.8, filed Dec. 21, 2011.

SEQUENCE LISTING

The instant application contains a Sequence Listing submitted via EFS-Web and hereby incorporated by reference in its entirety. Said ASCII copy, created on Jan. 7, 2019, is named P30785-US-2_Sequence_Listing.TXT, and is 10,290 bytes in size.

FIELD OF THE INVENTION

Herein is reported a method for the isolation (cloning, expression, and selection) of an antibody starting from a single antibody-producing B-cell, wherein the individual steps of the method are all performed in solution allowing for the identification of antibodies with the desired specificity.

BACKGROUND OF THE INVENTION

For obtaining cells secreting monoclonal antibodies the hybridoma technology developed by Koehler and Milstein is widely used. But in the hybridoma technology only a fraction of the B-cells obtained from an immunized experimental animal can be fused and propagated. The source of the B-cells is generally an organ of an immunized experimental animal such as the spleen.

Zubler et al. started in 1984 to develop a different approach for obtaining cells secreting monoclonal antibodies (see e.g. Eur. J. Immunol. 14 (1984) 357-363, J. Exp. Med. 160 (1984) 1170-1183). Therein the B-cells are obtained from the blood of the immunized experimental animal and co-cultivated with murine EL-4 B5 feeder cells in the presence of a cytokine comprising feeder mix. With this methodology up to 50 ng/ml antibody can be obtained after 10-12 days of co-cultivation.

Weitkamp, J.-H., et al., (J. Immunol. Meth. 275 (2003) 223-237) report the generation of recombinant human monoclonal antibodies to rotavirus from single antigen-specific B-cells selected with fluorescent virus-like particles. A method of producing a plurality of isolated antibodies to a plurality of cognate antigens is reported in US 2006/0051348. In WO 2008/144763 and WO 2008/045140 antibodies to IL-6 and uses thereof and a culture method for obtaining a clonal population of antigen-specific B cells are reported, respectively. A culture method for obtaining a clonal population of antigen-specific B-cells is reported in US 2007/0269868. Masri et al. (in Mol. Immunol. 44 (2007) 2101-2106) report the cloning and expression in E. coli of a functional Fab fragment obtained from single human lymphocyte against anthrax toxin. A method for preparing immunoglobulin libraries is reported in WO 2007/031550.

In WO 2010/056898 rapid expression and cloning of human monoclonal antibodies from memory B-cells is reported. A rapid and efficient single-cell manipulation method for screening antigen-specific antibody-producing cells from human peripheral blood is reported by Jin et al. (Jin, A., et al., Nature Medicine 15 (2009) 1088-1093). Lightwood et al. (Lightwood, D. J., et al., J. Immunol. Meth. 316 (2006) 133-143) report antibody generation through B-cell panning on antigen followed by in situ culture and direct RT-PCR on cells harvested en masse from antigen-positive wells.

SUMMARY OF THE INVENTION

In the method as reported herein the isolation of nucleic acid fragments or segments encoding antibody variable domains (light and heavy chain) and the insertion of the isolated nucleic acid fragments or segments in eukaryotic expression cassettes (one cassette each for the light and heavy chain, respectively) is performed without the intermediate isolation and analysis of clonal intermediate plasmids/cassettes. Thus, in the method as reported herein the intermediate cloning, isolation and analysis of intermediate plasmids/cassettes is not required, e.g. by analysis of isolated transformed E. coli cells, thus, resulting in a faster method.

One aspect as reported herein is a method for the isolation of nucleic acids encoding cognate variable domains of an antibody comprising the following steps:
  synthesizing single stranded cDNA using the RNA obtained from an antibody secreting B-cell as template in an RT-PCR,
  amplifying the variable domain encoding nucleic acids in a PCR and thereby isolating the nucleic acid fragments encoding the cognate variable domains of an antibody, whereby the PCR primer are removed after the PCR.

In one embodiment the method is performed without the isolation and analysis of intermediate nucleic acids.

One aspect as reported herein is a method for producing an antibody comprising the following step:
  cultivating a eukaryotic cell comprising a nucleic acid encoding an antibody, and
  recovering the antibody from the cell or the cultivation medium,
whereby the nucleic acid encoding the antibody is obtained by
  synthesizing single stranded cDNA using the RNA obtained from an antibody secreting B-cell as template in an RT-PCR,
  amplifying the variable domain encoding nucleic acid(s) in a PCR, and
  inserting the variable domain encoding nucleic acid(s) in one or more eukaryotic expression plasmids.

In one embodiment the PCR primer are removed after the PCR.

In one embodiment the method is performed without the isolation and analysis of intermediate nucleic acids.

One aspect as reported herein is a method for producing an antibody comprising the following step:
  cultivating a eukaryotic cell transfected with one or more expression plasmids encoding the antibody heavy and light chains whereby the one or more expression plasmids have been prepared from a pool of plasmid transformed E. coli cells, recovering the antibody from the cell or the cultivation medium.

One aspect as reported herein is a method for producing an antibody comprising the following step:
recovering the antibody from the cultivation medium of a eukaryotic cell comprising a nucleic acid encoding the antibody,
whereby the nucleic acid encoding the antibody is obtained by
amplifying cognate variable domain encoding nucleic acids from single stranded cDNA obtained from the RNA of an antibody secreting B-cell as template in a PCR, and
inserting the variable domain encoding nucleic acids in a eukaryotic expression plasmid by ligation independent cloning,
wherein a pool of nucleic acids encoding the antibody light and heavy chain variable domain, respectively, is used for the insertion.

In one embodiment the method comprises as first step:
synthesizing single stranded cDNA using the RNA obtained from an antibody secreting B-cell as template.

In one embodiment the PCR primer are removed after the PCR.

In one embodiment the method is performed without the isolation and analysis of intermediate nucleic acids.

One aspect as reported herein is a method for producing an antibody comprising the following step:
cultivating a eukaryotic cell transfected with an expression plasmid encoding the antibody, whereby the eukaryotic cell has been transfected with a pool of expression plasmids that has been prepared from a pool of plasmid transformed *E. coli* cells,
recovering the antibody from the cell or the cultivation medium.

In one embodiment the nucleic acid encoding the antibody is obtained by
amplifying cognate variable domain encoding nucleic acids from single stranded cDNA obtained from the RNA of an antibody secreting B-cell as template in a PCR, and
inserting the variable domain encoding nucleic acids in a eukaryotic expression plasmid by ligation independent cloning.

In one embodiment the method comprises as first step:
synthesizing single stranded cDNA using the RNA obtained from an antibody secreting B-cell as template.

In one embodiment the PCR primer are removed after the PCR.

In one embodiment the method is performed without the isolation and analysis of intermediate nucleic acids.

In one embodiment of all aspects the B-cell is a rabbit B-cell.

In one embodiment of all aspects the B-cell is a single deposited B-cell.

In one embodiment of all aspects the B-cell is cultivated for about 7 days.

In one embodiment of all aspects the B-cell and its progeny produces more than 20 ng/ml antibody in 7 days of co-cultivation with feeder cells starting from a single cell.

In one embodiment of all aspects the PCR primer have the nucleic acid sequences of SEQ ID NO: 5 and 6 or SEQ ID NO: 7 or 8.

In one embodiment of all aspects the nucleic acid fragments are inserted into the expression plasmid by sequence and ligation independent cloning.

In one embodiment of all aspects about 300 ng nucleic acid is used in the insertion reaction.

In one embodiment of all aspects a pool of nucleic acids is used for the insertion.

In one embodiment of all aspects the expression plasmid is obtained by sequence and ligation independent cloning of the variable domain encoding nucleic acid into a variable domain free amplified expression plasmid.

In one embodiment of all aspects the plasmid is linearized prior to the amplification.

DETAILED DESCRIPTION OF THE INVENTION

Definitions

"Affinity" refers to the strength of the total sum of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); single domain antibodies; and multispecific antibodies formed from antibody fragments.

The "class" of an antibody refers to the type of constant domain or constant region possessed by its heavy chain. E.g. there are five major classes of antibodies in the human: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "cognate pair of antibody variable domains" denotes a pair of antibody variable domains that is obtained from a single antibody secreting B-cell, i.e. which has been generated as pair during the immune response of a mammal due to the contact with an immunogenic molecule or which have been assembled randomly during a display approach.

An "effective amount" of an agent, e.g., a pharmaceutical formulation, refers to an amount effective, at dosages and for periods of time necessary, to achieve the desired therapeutic or prophylactic result.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantified by qPCR or RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantified by various methods, e.g. by ELISA, by assaying the biological activity of the polypeptide, or by employing assays that are independent of such activity, such as Western blotting or radioimmunoassay, using immunoglobulins that recognize and bind to the polypeptide (see Sambrook, et al., (1989), supra).

An "expression cassette" denotes a construct that contains the necessary regulatory elements, such as promoter and polyadenylation site, for expression of at least the contained nucleic acid in a cell.

The term "expression machinery" denotes the sum of the enzymes, cofactors, etc. of a cell that is involved in the steps of gene expression beginning with the transcription step of a nucleic acid or gene (i.e. also called "gene expression machinery") to the post-translational modification of the polypeptide encoded by the nucleic acid. The expression machinery e.g. comprises the steps of transcription of DNA into pre-mRNA, pre-mRNA splicing to mature mRNA, translation into a polypeptide of the mRNA, and post translational modification of the polypeptide.

An "expression plasmid" is a nucleic acid providing all required elements for the expression of the comprised structural gene(s) in a host cell. Typically, an expression plasmid comprises a prokaryotic plasmid propagation unit, e.g. for *E. coli*, comprising an origin of replication, and a selectable marker, a eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The terms "host cell", "host cell line", and "host cell culture" are used interchangeably and refer to cells into which exogenous nucleic acid has been introduced, including the progeny of such cells. Host cells include "transformants" or "transfectants" and "transformed cells" and "transfected cells" which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is selected from the group of mammalian cells comprising CHO cells (e.g. CHO K1, CHO DG44), BHK cells, NS0 cells, Sp2/0 cells, HEK 293 cells, HEK 293 EBNA cells, PER.C6® cells, and COS cells.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "individual" or "subject" is a vertebrate. In one embodiment the vertebrate is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In other embodiments the individual or subject is a rabbit.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "peptide linker" denotes amino acid sequences of natural and/or synthetic origin. They consist of a linear amino acid chain wherein the 20 naturally occurring amino acids are the monomeric building blocks. The peptide linker has a length of from 1 to 50 amino acids, in one embodiment between 1 and 28 amino acids, in a further embodiment between 2 and 25 amino acids. The peptide linker may contain repetitive amino acid sequences or sequences of naturally occurring polypeptides. The linker has the function to ensure that polypeptides conjugated to each other can perform their biological activity by allowing the polypeptides to fold correctly and to be presented properly. In one embodiment the peptide linker is rich in glycine, glutamine, and/or serine residues. These residues are arranged e.g. in small repetitive units of up to five amino acids, such as GS (SEQ ID NO: 1), GGS (SEQ ID NO: 2), GGGS (SEQ ID NO: 3), and GGGGS (SEQ ID NO: 4). The small repetitive unit may be repeated for one to five times. At the amino- and/or carboxy-terminal ends of the multimeric unit up to six additional arbitrary, naturally occurring amino acids may be added. Other synthetic peptidic linkers are composed of a single amino acid, which is repeated between 10 to 20 times and may comprise at the amino- and/or carboxy-terminal end up to six additional arbitrary, naturally occurring amino acids. All peptidic linkers can be encoded by a nucleic acid molecule and therefore can be recombinantly expressed. As the linkers are themselves peptides, the polypeptide connected by the linker are connected to the linker via a peptide bond that is formed between two amino acids.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "polypeptide" is a polymer consisting of amino acids joined by peptide bonds, whether produced naturally or synthetically. Polypeptides of less than about 25 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

A "structural gene" denotes the region of a gene without a signal sequence, i.e. the coding region.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J., et al., Kuby Immunology, 6th ed., W. H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "variant" denotes variants of a parent amino acid sequence that comprises one or more amino acid substitution, addition, or deletion.

The term "vector" denotes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

General Steps of the Method as Reported Herein

Immunization

Often non-human animals, such as mice, rabbits, hamster and rats, are used as animal model for evaluating antibody based therapies. Also possible is to use the B-cells of a human that survived a specific disease, that suffers from a chronic disease, or that was recently vaccinated against a specific disease.

In the method as reported herein B-cells obtained from e.g. mouse, rat, hamster, rabbit, sheep, llama, or human can be used. In one embodiment the mouse is an NMRI-mouse or a balb/c-mouse. In another embodiment the hamster is selected from Armenian hamster (*Cricetulus migratorius*), Chinese hamster (*Cricetulus griseus*), and Syrian hamster (*Mesocricetulus auratus*). In a specific embodiment the hamster is the Armenia hamster. In one embodiment the rabbit is selected from New Zealand White (NZW) rabbits, Zimmermann-rabbits (ZIKA), Alicia-mutant strain rabbits, basilea mutant strain rabbits, transgenic rabbits with a human immunoglobulin locus, rabbit IgM knock-out rabbits, and cross-breeding thereof.

In one embodiment the experimental animals, e.g. mice, hamsters, rats and rabbits, chosen for immunization are not older than 12 weeks.

Source and Isolation of B-Cells

The blood of an experimental animal or a human provides a high diversity of antibody producing B-cells. The therefrom obtained B-cells secrete antibodies that have almost no identical or overlapping amino acid sequences within the CDRs, thus, show a high diversity.

In one embodiment the B-cells of an experimental animal or a human, e.g. from the blood, are obtained from 4 days after immunization until at least 9 days after immunization or the most recent boost immunization. This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

B-cells from the blood of an experimental animal or human may be obtained with any method known to a person skilled in the art. For example, density gradient centrifugation (DGC) or red blood cell lysis (lysis) can be used. Density gradient centrifugation compared to lysis provides for a higher overall yield, i.e. number of B-cell clones. Additionally from the cells obtained by density gradient centrifugation a larger number of cells divides and grows in the co-cultivation step. Also the concentration of secreted antibody is higher compared to cells obtained with a different method. Therefore, in one embodiment the provision of a population of B-cells is by density gradient centrifugation.

Isolation of mRNA, Cloning, and Sequencing

From the B-cells the total mRNA can be isolated and transcribed to cDNA. With specific primers, the cognate VH- and VL-region encoding nucleic acids can be amplified. With the method as reported herein almost no identical sequences will be obtained. Thus, the method provides for highly diverse antibodies binding to the same antigen.

In one embodiment the methods as reported herein are for producing an antibody comprising cognate antibody variable domains. In one embodiment the cognate antibody variable domains are from a single B-cell.

Primer can be provided for the amplification of the VH-encoding nucleic acid obtained from B-cells of the NMRI-mouse, the Armenian Hamster, the Balb/c-mouse, the Syrian hamster, the rabbit, the rat, the sheep, the llama, and the human.

One aspect as reported herein is a method for producing an antibody comprising the following steps:
a) depositing single (mature) B-cells (obtained from the blood or a lymphoid organ of an experimental animal or a human) from a stained population of B-cells (in one embodiment the B-cells are stained with one to three, or two to three fluorescence dyes) in individual containers (in one embodiment is the container a well of a multi well plate),
b) cultivating the deposited individual B-cells in the presence of feeder cells and a feeder mix (in one embodiment the feeder cells are EL-4 B5 cells, in one embodiment the feeder mix is natural TSN (supernatant of a cultivation of thymocytes of an experimental animal of the same species from which the B-cells are derived), in one embodiment the feeder mix is a synthetic feeder mix),
c) determining the amino acid sequence of the variable light and heavy chain domains of specifically binding antibodies by a reverse transcription PCR (RT-PCR) and nucleotide sequencing, and thereby obtaining a monoclonal antibody variable light and heavy chain domain encoding nucleic acid,
d) cultivating a cell comprising a nucleic acid encoding the variable light and heavy chain in individual HC and LC expression cassettes and recovering the antibody from the cell or the cell culture supernatant and thereby producing an antibody.

In one embodiment the method comprises the following steps:
a) providing a population of (mature) B-cells (obtained from the blood or a lymphoid organ of an experimental animal or a human),
b) staining the cells of the population of B-cells with at least one fluorescence dye (in one embodiment with one to three, or two to three fluorescence dyes),
c) depositing single cells of the stained population of B-cells in individual containers (in one embodiment is the container a well of a multi well plate),
d) cultivating the deposited individual B-cells in the presence of feeder cells and a feeder mix (in one embodiment the feeder cells are EL-4 B5 cells, in one embodiment the feeder mix is natural TSN (supernatant of a cultivation of thymocytes of an experimental animal of the same species from which the B-cells are derived), in one embodiment the feeder mix is a synthetic feeder mix),
e) determining the binding specificity of the antibodies secreted in the cultivation of the individual B-cells,
f) isolating the total RNA of a B-cell secreting an antibody with the desired binding specificity,
g) performing with the polyA$^+$ extracted mRNA an RT-PCR with primer specific for the light and heavy chain variable domains,
h) determining the amino acid sequence of the variable light and heavy chain domains of specifically binding antibodies,
i) introducing the monoclonal antibody light and heavy chain variable domain encoding nucleic acids in respective expression cassettes for the expression of an antibody,
j) introducing the nucleic acid into a cell,
k) cultivating the cell and recovering the antibody from the cell or the cell culture supernatant and thereby producing an antibody.

Specific Embodiments

In the method as reported herein the isolation of nucleic acid segments encoding antibody variable domains (light and heavy chain) and the insertion of the isolated nucleic acid segments in eukaryotic expression plasmids (one expression cassette each for the light and heavy chain, respectively) is performed without the intermediate isolation and analysis of clonal intermediate plasmids. Thus, in the method as reported herein the intermediate cloning, isolation and analysis of intermediate cassettes/plasmids is not required, e.g. by analysis of isolated transformed *E. coli* cells. In one embodiment the methods as reported herein are performed without the intermediate isolation and analysis of clonal intermediate plasmids.

It has been found that in the methods as reported herein the respective nucleic acid fragments encoding the heavy and light chain variable domain of an antibody as obtained after a specific polymerase chain reaction can be inserted into eukaryotic expression constructs, one for each chain, respectively, and expanded without the requirement of intermediate plating in order to pick and analyze plasmid DNA obtained from single colonies of transformed bacteria.

Typically, a restriction endonuclease cleavage site is engineered into both sense and antisense primer, respectively, allowing the insertion of the PCR fragments into an appropriately designed expression vector. However, the relatively high promiscuity of the ligation process results in a comparatively high number of individual plasmid clones containing no inserted nucleic acid fragment ("empty vector"), containing a nucleic acid fragment inserted in the wrong direction, or containing only an incomplete fragment of the nucleic acid to be cloned. This problem usually is solved by plating the ligation reaction on solid media in such a way that individual bacterial colonies can be isolated. Several of these bacterial colonies (clones) are then picked and grown in liquid culture, and the respective plasmids contained in these clones are analyzed for orientation and completeness of the inserted nucleic acid fragments. One of the correctly assembled plasmids is then selected and further amplified for e.g. the recombinant expression of the encoded polypeptides. While being a multi time-tested method for the cloning of a small, limited number of DNA fragments, this method is cumbersome, laborious and time-consuming when the cloning of a large number of nucleic acid fragments is required because of the necessity to pick, amplify and analyze the plasmid DNA derived from single colonies as specified above.

Thus, it has been found that the entire workflow from the initial generation and cloning of the DNA fragments into expression vectors until the recombinant expression of the polypeptides encoded by the respective plasmid vectors can be performed in one coherent workflow without the need for intermediate isolation and analysis of single colonies. It has been found that it is advantageous to employ ligation-independent cloning as a means to improve the above-outlined workflow. Thus, in one embodiment the inserting in the eukaryotic expression plasmid is by ligation-independent cloning.

Ligation-independent cloning as such is not necessarily more efficient than conventional cloning via restriction and ligation in the sense that the number of individual colonies obtained is significantly higher. But since this method is based on sequence-specific annealing of complementary single-stranded DNA overhangs rather than enzymatic ligation for the assembly of complex molecules, this method comprises significantly longer complementary single-stranded ends of the individual nucleic acid fragments to be cloned. Thus, typically single-stranded nucleotide overhangs encompassing 15-30 nucleotides are used in ligation-independent cloning versus 2-4 nucleotides generated by restriction endonucleases. In addition, since no ligase enzyme is present in ligation-independent cloning, the re-ligation of empty vector cannot occur. Consequently, the proportion of correctly inserted nucleic acid fragments into a vector with regard to size, orientation and integrity is increased while simultaneously the proportion of "empty", re-ligated vector containing no inserted nucleic acid fragment at all and the frequency of plasmids containing defective DNA fragments are decreased in ligation-independent cloning. Indeed, the analysis of cloning products obtained by ligation-independent cloning showed that over 90% of all plasmid molecules contained a full length inserted nucleic acid in the correct orientation.

It has been found, since the vast majority of all plasmid molecules thus generated contains correctly inserted nucleic acid fragments, the entire pool of transformed bacteria can be grown and expanded in liquid culture without the need for the intermediate steps of plating the transformed bacteria on solid media, isolation of single colonies, and analysis and isolation of individual plasmid DNA clones. With the method as reported herein a reduction in time and labor required can be achieved. With this improved method an automatization of the process can be performed.

The difference between the classical approach and the method as reported herein is outlined in the following Table 1. It can be seen that the number of steps required can be reduced by more than 40%.

TABLE 1

| classical approach | ligation-independent approach |
|---|---|
| generate and purify PCR fragment | generate and purify PCR fragment |
| prepare vector for ligation | prepare vector for annealing |
| restriction enzyme treatment | T4-DNA polymerase treatment |
| purify DNA insert | — |
| ligation of fragment with prepared vector | annealing of fragment with prepared vector |
| transformation into competent bacteria | transformation into competent bacteria |
| plate and grow on solid media | grow in bulk in liquid culture |
| pick individual colonies (clones) | — |
| grow clones in liquid culture | — |
| isolate plasmid DNA from colonies | — |
| analyze plasmid DNA from colonies | — |
| grow correct clone in liquid culture | — |
| isolate plasmid DNA | isolate plasmid DNA |
| transfect eukaryotic cells with expression plasmid | transfect eukaryotic cells with expression plasmid |

— denotes: not needed to be performed.

The method as reported herein can be performed with B-cells obtained at any point in time after the immunization of an experimental animal.

The method as reported herein can be performed early after immunization so that first antibody-encoding nucleic acids can be isolated as early as three weeks after the first immunization of an experimental animal.

The method as reported herein is especially suited for the isolation of variable domain-encoding nucleic acid fragments from rabbit B-cells since hybridomas derived from rabbit B-cells result in poorly producing clones. In addition the isolation of variable domain-encoding nucleic acid fragments from rabbit-derived hybridomas is interfered by the endogenous light chain transcript of the commonly used myeloma fusion partner.

The method as reported herein is faster compared to the classical approach.

In one embodiment the B-cell is a human B-cell, or a mouse B-cell, or a rat B-cell, or a rabbit B-cell, or a hamster B-cell, or a B-cell derived from a transgenic animal. In one embodiment the B-cell is a rabbit B-cell, or a human B-cell, or a B-cell derived from a transgenic animal.

A transgenic animal is an animal in which the endogenous Ig locus has been inactivated or removed and which comprises an active or functional human Ig locus.

In one embodiment the B-cell is a B-cell of an immunized experimental animal.

In one embodiment the B-cell is a B-cell of an immunized human individual, or a human individual that has survived a disease, or a human that is suffering from a chronic disease.

In one embodiment the B-cell is a single deposited antibody secreting B-cell.

In one embodiment the B-cell is cultivated for 6 to 8 generations.

In one embodiment the B-cell is cultivated until about 10 to about 100 cells are obtained.

In one embodiment the B-cell produces about 10 ng/ml antibody after 7 days of cultivation. In one embodiment the B-cell produces about 20 ng/ml antibody after 7 days of cultivation.

It has been found, that if a B-cell producing less than 10 ng/ml antibody is used the method as reported herein can also be performed but with lesser amplification efficiency.

In one embodiment the nucleic acid fragments encoding the variable domains are isolated and/or amplified by RT-PCR.

In one embodiment the nucleic acid fragment encoding the variable light chain domain and the nucleic acid fragment encoding the variable heavy chain domain are cognate nucleic acids. In one embodiment the nucleic acid fragments encoding the heavy and light chain variable domains are isolated from the same cell and/or their progeny.

In one embodiment the B-cell is a rabbit B-cell and the nucleic acid encoding the variable heavy chain domain is isolated with the primer of SEQ ID NO: 5 (AAGCTTGC-CACCATGGAGACTGGGCTGCGCTGGCTTC) and SEQ ID NO: 6 (CCATTGGTGAGGGTGCCCGAG).

In one embodiment the B-cell is a rabbit B-cell and the nucleic acid encoding the variable light chain domain is isolated with the primer of SEQ ID NO: 7 (AAGCTTGC-CACCATGGACAYGAGGGCCCCCACTC) and SEQ ID NO: 8 (CAGAGTRCTGCTGAGGTTGTAGGTAC).

In analogy, primer for amplification of e.g. rat, mouse or human immunoglobulin V-domain gene segments can be designed. In one embodiment the primer are directed to sequences in the first framework region. See e.g. van Dongen, J. J. M., et al. Leukemia 17 (2003) 2257; Widhopf, G. F., et al. Blood 111 (2008) 3137; Fais, F., et al. J. Clin. Invest. 102 (1998) 1515 for human B-cells; see e.g. Wang, Z., et al. J. Immunol. Methods. 233 (2000) 167; Jones, T. and Bendig, M., Bio/Technology 90 (1991) 88 for murine B-cells.

In one embodiment the amplified nucleic acid is used without purification after removal of the PCR primer.

In one embodiment the amplified nucleic acid is used without purification after removal of all PCR primer.

In one embodiment the nucleic acid fragments encoding the variable domains are inserted by sequence and ligation independent cloning (SLIC) into the eukaryotic expression plasmid.

In one embodiment the insertion does not require restriction enzyme cleavage sites.

In one embodiment the insertion does not require a phosphatase treatment of the nucleic acid fragment.

In one embodiment the integration does not require an enzymatic ligation.

In one embodiment the T4 DNA polymerase is employed in the absence of nucleotides for generating single strand extensions.

In one embodiment about 200 ng nucleic acid (=PCR product) is used in the insertion step. In one embodiment about 100 ng nucleic acid is used. In one embodiment about 50 ng nucleic acid is used.

In one embodiment the ratio of plasmid to nucleic acid is about 1:2 (w/w). In one embodiment about 100 ng plasmid and about 200 ng nucleic acid are used in the insertion step.

In one embodiment the method is a high throughput method.

In one embodiment the method is performed in parallel for at least ten B-cell clones.

In one embodiment the efficiency of the method starting from the amplification product to the recombinantly expressed antibody is more than 50%.

It has been found that it is especially suited to employ in the method as reported herein a pool of nucleic acids obtained from a pool of E. coli cells containing the assembled and/or amplified antibody expression plasmids for the antibody light and heavy chain, respectively. Therewith potential errors during the nucleic acid amplification of single clones can be leveled, or masked, or reduced to background level.

In one embodiment the nucleic acid is a pool of nucleic acids obtained from a pool of E. coli cells containing the assembled and/or amplified antibody expression plasmids for the antibody light and heavy chain, respectively.

It has been found that the PCR primers have to be removed or likewise the PCR product has to be purified prior to the sequencing step. This separation/purification increases the sequencing efficiency.

It has been found that it is advantageous to amplify the backbone of the plasmid excluding the nucleic acids encoding the variable domains.

In one embodiment the plasmid from which the vector (or plasmid) backbone is amplified is linearized prior to the amplification. In one embodiment the plasmid is linearized by the use of two or more different restriction enzymes prior to the amplification.

In one embodiment the amplification product is digested with a methylation dependent restriction enzyme, e.g. DpnI.

This allows for more flexibility and efficiency in the subsequent method steps.

In one embodiment the method comprises the following steps:
   total RNA extraction from antibody-producing B-cells of an immunized experimental animal,
   single stranded cDNA synthesis/reverse transcription of the extracted polyA$^+$ mRNA,
   PCR with species specific primer,
   removal of the PCR primer/purification of the PCR product,
   optionally sequencing of the PCR product,
   T4 polymerase incubation of the PCR product,
   linearization and amplification of plasmid-DNA,
   T4 polymerase incubation of the amplified plasmid-DNA,
   sequence and ligation independent cloning of the variable domain encoding nucleic acid into the amplified plasmid,
   preparation of plasmid from pool of plasmid transformed E. coli cells,
   transfection of eukaryotic cells with plasmid prepared in the previous step,
   expression of antibody.

In one embodiment the light chain encoding plasmid backbone DNA is amplified with the primer of SEQ ID NO: 9 (GTACCTACAACCTCAGCAGCACTCTG) and SEQ ID NO: 10 (CCCTCRTGTC-CATGGTGGCAAGCTTCCTCTGTGTTCAGTGCT G).

In one embodiment the heavy chain encoding plasmid backbone DNA is amplified with the primer of SEQ ID NO: 11 (TGGGAACTCGGGCACCCTCACCAATGG) and SEQ ID NO: 12 (GCCCAGTCTC-CATGGTGGCAAGCTTCCTCTGTGTTCAGT GCTG).

The following examples and sequence listing are provided to aid the understanding of the present invention, the true scope of which is set forth in the appended claims. It is understood that modifications can be made in the procedures set forth without departing from the spirit of the invention.

SEQUENCES

SEQ ID NO: 1 linker peptide 1
SEQ ID NO: 2 linker peptide 2
SEQ ID NO: 3 linker peptide 3
SEQ ID NO: 4 linker peptide 4
SEQ ID NO: 5 heavy chain variable domain isolation primer 1 (rb-VH3-23-Slic-s001 primer)
SEQ ID NO: 6 heavy chain variable domain isolation primer 2 (rb-CH1rev-2 primer)
SEQ ID NO: 7 light chain variable domain isolation primer 1 (rb-V-kappa-Slic-s001 primer)
SEQ ID NO: 8 light chain variable domain isolation primer 2 (rbCk1-rev2 primer)
SEQ ID NO: 9 light chain plasmid amplification primer 1 (8011-Slic-s001 primer)
SEQ ID NO: 10 light chain plasmid amplification primer 2 (8000-Slic-as002 primer)
SEQ ID NO: 11 heavy chain plasmid amplification primer 1 (8001-Slic-s001 primer)
SEQ ID NO: 12 heavy chain plasmid amplification primer 2 (8001-Slic-as002 primer)
SEQ ID NO: 13 rb-V-kappa-HindIIIs primer
SEQ ID NO: 14 rb-C-kappa-NheIas primer
SEQ ID NO: 15 rb-CH1rev-1 primer
SEQ ID NO: 16 rbVH3-23for3 primer
SEQ ID NO: 17 bcPCR-huCgamma-rev primer
SEQ ID NO: 18 bcPCR-FHLC-leader-fw primer
SEQ ID NO: 19 bcPCR-huCkappa-rev primer
SEQ ID NO: 20 bcPCR-hu-HC-10600-SLIC-as primer
SEQ ID NO: 21 bcPCR-hu-HC-10600-SLIC-s primer
SEQ ID NO: 22 bcPCR-hu-LC-10603-SLIC-s primer
SEQ ID NO: 23 bcPCR-hu-LC-10603-SLIC-as primer
SEQ ID NO: 24 SLIC-hu-VHuniversal-for primer
SEQ ID NO: 25 SLIC-hu-VH6-for primer
SEQ ID NO: 26 hu-CH1gamma-rev primer
SEQ ID NO: 27 SLIC-huVk2-for primer
SEQ ID NO: 28 SLIC-huVk3-for primer
SEQ ID NO: 29 SLIC-huVk5-for primer
SEQ ID NO: 30 SLIC-huVk7-for primer
SEQ ID NO: 31 SLIC-huVk8-for primer
SEQ ID NO: 32 SLIC-huVk1long-for primer
SEQ ID NO: 33 SLIC-huVk2longw-for primer
SEQ ID NO: 34 huCk-rev primer
SEQ ID NO: 35 SLIC-huVl1-for primer
SEQ ID NO: 36 SLIC-huVl2-for primer
SEQ ID NO: 37 SLIC-huVl3-for primer
SEQ ID NO: 38 SLIC-huVl4-for primer
SEQ ID NO: 39 SLIC-huVl5-for primer
SEQ ID NO: 40 SLIC-huVl6-for primer
SEQ ID NO: 41 SLIC-huVl7-for primer
SEQ ID NO: 42 SLIC-huVl8-for primer
SEQ ID NO: 43 SLIC-huVl9-for primer
SEQ ID NO: 44 SLIC-huVlambda10-for primer
SEQ ID NO: 45 huC1-1-rev primer
SEQ ID NO: 46 huIg-PCR-vectorprimer-as
SEQ ID NO: 47 huIg-PCR-vectorprimer-VH-s
SEQ ID NO: 48 huIg-PCR-vectorprimer-as kappa
SEQ ID NO: 49 huIg-PCR-vectorprimer-VK-s
SEQ ID NO: 50 huIg-PCR-vectorprimer-as lambda
SEQ ID NO: 51 huIg-PCR-vectorprimer-VL-s

EXAMPLES

Example 1

Cloning and Expression of Cognate Antibody Variable Region Gene Segments a) RNA Extraction Cells were lysed by adding of 100 µl RLT buffer containing 10 µl/ml 2-mercaptoethanol and mixing by repeated pipetting. The lysate was either used directly for RNA isolation or stored frozen at −20° C. until RNA preparation. RNA was prepared using the Total RNA Isolation Kit NucleoSpin (Machery & Nagel) according to the manufacturer's instructions b) First Strand cDNA Synthesis cDNA was generated by reverse transcription of mRNA using the Super Script III first-strand synthesis SuperMix (Invitrogen) according to the manufacturer's instructions. In a first step 6 µl of the isolated mRNA was mixed with 1 µl annealing buffer and 1 µl (50 µM) oligo dT, incubated for 5 minutes at 65° C. and thereafter immediately placed on ice for about 1 minute. Subsequently while still on ice 10 µl 2× First-Strand Reaction Mix and SuperScript™ III/RNase-OUT™ Enzyme Mix were added. After mixing the reaction was incubated for 50 minutes at 50° C. The reaction was terminated by incubation at 85° C. for 5 minutes. After termination the reaction mix was placed on ice.

c) Polymerase Chain Reaction (PCR)

The polymerase chain reaction was carried out using AccuPrime Pfx SuperMix (Invitrogen) according to the manufacturer's instructions. Light chain and heavy chain variable regions were amplified in separate reactions. PCR-primer (0.2 µM/reaction) with 25 bp overlaps to target antibody expression vectors were used. After the PCR 8 µl of the PCR reaction mixture were used for analysis on 48-well eGels (Invitrogen).

d) Purification of PCR Products

Residual PCR primer were removed using the Nucleo-Spin® 96 Extract II kit (Machery & Nagel) according to the manufacturer's instructions.

e) Sequence Determination

The DNA sequences encoding the variable domains of the antibody heavy and light chains were obtained by sequencing the PCR products.

f) Preparation of Plasmid-DNA

The plasmid DNA to be used as recipient for the cloning of the PCR products encoding the antibody heavy and light chain variable domains was first linearized by restriction enzyme digestion. Subsequently, the linearized plasmid DNA was purified by preparative agarose electrophoresis and extracted from the gel (QIAquick Gel Extraction Kit/ Qiagen). This purified plasmid DNA was added to a PCR-protocol as template using primer overlapping (by 20-25 bp) with the PCR-products to be cloned. The PCR was carried out using AccuPrime Pfx SuperMix (Invitrogen).

g) Cloning

The PCR-products were cloned into expression vectors using a "site and ligation independent cloning" method (SLIC) which was described by Haun, R. S., et al. (Bio-Techniques 13 (1992) 515-518) and Li, M. Z., et al. (Nature Methods 4 (2007) 251-256). Both purified vector and insert were treated with 0.5 U T4 DNA polymerase (Roche Applied Sciences, Mannheim, Germany) per 1 μg DNA for 45 minutes at 25° C. in the absence of dNTPs to generate matching overhangs. The reaction was stopped by adding $\frac{1}{10}^{th}$ of the reaction volume of a 10 mM dCTP Solution (Invitrogen). The T4 treated vector and insert DNA fragments were combined with a plasmid:insert ratio of 1:2 (w/w) (e.g. 100 ng:200 ng) and recombined by adding RecAProtein (New England Biolabs) and 10× RecA Buffer for 30 minutes at 37° C. Subsequently, 5 μl of each of the generated heavy chain and light chain expression plasmid was used to transform MultiShot Strip Well TOP 10 Chemically Competent E. coli cells (Invitrogen) using a standard chemical transformation protocol. After regeneration (shaking for 45 minutes at 37° C. of the transformed E. coli cells) the entire transformation mixture was transferred into DWP 96 (deep well plates) containing 2 ml of LB medium supplemented with ampicillin per well. The cells were incubated in a shaker for 20 hours at 37° C. In the following step the plasmid DNA encoding the immunoglobulin heavy- and light chains was purified using the NucleoSpin 96 Plasmid Mini Kit (Macherey & Nagel), digested with selected restriction enzymes, and analyzed on 48-well eGels (Invitrogen). In parallel, glycerol stocks were prepared for storage.

h) Transfection and Expression of Recombinant Antibodies in Eukaryotic Cells

HEK293 cells were grown with shaking at 120 rpm in F17-medium (Gibco) at 37° C. in an atmosphere containing 8% $CO_2$. Cells were split the day before transfection and seeded at a density of 0.7-0.8×10$^6$ cells/ml. On the day of transfection, 1-1.5×10$^6$ HEK293 cells in a volume of 2 ml were transfected with 0.5 μg HC plasmid plus 0.5 μg LC plasmid, suspended in 1 μl 293-free medium (Novagen) and 80 μl OptiMEM® medium (Gibco) in 48 well deep well plates. Cultures were incubated for 7 days at 180 rpm at 37° C. and 8% $CO_2$. After 7 days the culture supernatants were harvested, filtered and analyzed for antibody content and specificity.

Example 2

B-Cell Productivity vs. Amplification Efficiency

It has been found that B-cells to be used in the method as reported herein have to be selected based on the expression yield (antibody titer) obtained by the cultivation of the single deposited B-cell in the presence of feeder cells, e.g. EL4-B5 cells and Zubler mix. The obtained expression yield has to be above a specific threshold value as can be seen from the following Table 2.

TABLE 2

|  | rabbit IgG [ng/ml] | % HC sequences | % LC sequences |
| --- | --- | --- | --- |
| Experiment 1 | <20 ng/ml | 0% (0/14) | 0% (0/14) |
| Experiment 2 | >20 ng/ml | 85% (52/61) | 85% (52/61) |

Successful sequence generation depending on rabbit IgG concentration in single cell cultivation supernatant.

Example 3

Primer
Primer For B-Cell PCR of B-Cells Expressing Rabbit Antibodies

```
primer set 1:
LC-primer
-rb-V-kappa-HindIIIs (SEQ ID NO: 13):
GATTAAGCTTATGGACAYGAGGGCCCCCACTC -rb-C-kappa-NheIas (SEQ ID NO: 14):
GATCGCTAGCCCTGGCAGGCGTCTCRCTCTAACAG HC-primer
-rb-CH1rev-1 (SEQ ID NO: 15):
GCAGGGGGCCAGTGGGAAGACTG -rbVH3-23for3 (SEQ ID NO: 16):
CACCATGGAGACTGGGCTGCGCTGGCTTC primer set 2:
LC-primer
-rb-V-kappa-Slic-s001 (SEQ ID NO: 18):
AAGCTTGCCACCATGGACAYGAGGGCCCCCACTC -rbCk1-rev2 (SEQ ID NO: 19):
CAGAGTRCTGCTGAGGTTGTAGGTAC HC-primer
-rb-VH3-23-Slic-s001 (SEQ ID NO: 20):
AAGCTTGCCACCATGGAGACTGGGCTGCGCTGGCTTC -rb-CH1rev-2 (SEQ ID NO: 21):
CCATTGGTGAGGGTGCCCGAG
```

Primer For Amplification of Heavy Chain Expression Plasmid Backbone:

```
-8001-Slic-s001 (SEQ ID NO: 22):
TGGGAACTCGGGCACCCTCACCAATGG

-8001-Slic-as002 (SEQ ID NO: 23):
GCCCAGTCTCCATGGTGGCAAGCTTCCTCTGTGTTCAGTGCTG
```

Primer For Amplification of Kappa Light Chain Expression Plasmid Backbone:

```
-8011-Slic-s001 (SEQ ID NO: 24):
GTACCTACAACCTCAGCAGCACTCTG

-8000-Slic-as002 (SEQ ID NO: 25):
CCCTCRTGTCCATGGTGGCAAGCTTCCTCTGTGTTCAGTGCTG
```

Primer For B-Cell PCR of Rabbit B-Cells Expressing Human Antibodies (Derived From Transgenic Rabbit)
Primer For Amplification of Heavy Chain Variable Domains

```
HC-Up
-rb-VH3-23-Slic-s001 (SEQ ID NO: 20):
AAGCTTGCCACCATGGAGACTGGGCTGCGCTGGCTTC -bcPCR-huCgamma-rev (SEQ ID NO: 17):
CCCCCAGAGGTGCTCTTGGA
```

Primer For Amplification of Light Chain Variable Domains

```
-bcPCR-FHLC-leader-fw (SEQ ID NO: 18):
ATGGACATGAGGGTCCCCGC

-bcPCR-huCkappa-rev (SEQ ID NO: 19):
GATTTCAACTGCTCATCAGATGGC
```

Primer For the Amplification of Heavy Chain Plasmid Backbone:

```
-bcPCR-hu-HC-10600-SLIC-as (SEQ ID NO: 20):
CAGCCCAGTCTCCATGGTGGCAAGCTTCCTCTGTGTTCAGTGCTG

-bcPCR-hu-HC-10600-SLIC-s (SEQ ID NO: 21):
CTCCAAGAGCACCTCTGGGGGCACAG
```

Primer For the Amplification of Kappa Light Chain Plasmid Backbone:

```
-bcPCR-hu-LC-10603-SLIC-s (SEQ ID NO: 22):
GCCATCTGATGAGCAGTTGAAATC

-bcPCR-hu-LC-10603-SLIC-as (SEQ ID NO: 23):
GCGGGGACCCTCATGTCCATGGTGGCAAGCTTCCTCTG
```

Primer For B-Cell PCR of B-Cells From Human Donors

Primer For Amplification of Heavy Chain Variable Domains

```
-SLIC-hu-VHuniversal-for (SEQ ID NO: 24):
AGCAACAGCTACAGGTGTGCATTCCGAGGTGCAGCTGKTGSAGTCTGS -SLIC-hu-VH6-for (SEQ ID NO: 25):
AGCAACAGCTACAGGTGTGCATTCCCAGGTRCAGCTGCAGSAGTC -hu-CHI gamma-rev (SEQ ID NO: 26):
GTCCACCTTGGTGTTGCTGGGCTT
```

Primer For Amplification of Kappa Light Chain Variable Domains

```
-SLIC-huVk2-for (SEQ ID NO: 27):
TAGCAACAGCTACAGGTGTGCATTCCGATGTTGTGATGACTCAGTCT -SLIC-huVk3-for (SEQ ID NO: 28):
TAGCAACAGCTACAGGTGTGCATTCCGAAATTGTGWTGACRCAGTCT -SLIC-huVk5-for (SEQ ID NO: 29):
TAGCAACAGCTACAGGTGTGCATTCCGACATCGTGATGACCCAG -SLIC-huVk7-for (SEQ ID NO: 30):
TAGCAACAGCTACAGGTGTGCATTCCGAAATTGTGCTGACTCAGTCT -SLIC-huVk8-for (SEQ ID NO: 31):
TAGCAACAGCTACAGGTGTGCATTCCGAWRTTGTGMTGACKCAGTCTCC -SLIC-huVk1long-for (SEQ ID NO: 32):
TAGCAACAGCTACAGGTGTGCATTCCGACATCCRGWTGACCCAGTCT -SLIC-huVk2longw-for (SEQ ID NO: 33):
TAGCAACAGCTACAGGTGTGCATTCCGATRTTGTGATGACYCAGWCT -huCk-rev (SEQ ID NO: 34):
ACACTCTCCCCTGTTGAAGCTC
```

Primer For Amplification of Lambda Light Chain Variable Domains

```
-SLIC-huVl1-for (SEQ ID NO: 35):
TAGCAACAGCTACAGGTGTGCATTCCCAGTCTGTGYTGACKCAG -SLIC-huVl2-for (SEQ ID NO: 36):
TAGCAACAGCTACAGGTGTGCATTCCCAGTCTGCCCTGACTCAG -SLIC-huVl3-for (SEQ ID NO: 37):
TAGCAACAGCTACAGGTGTGCATTCCTCCTATGAGCTGAYWCAG -SLIC-huVl4-for (SEQ ID NO: 38):
TAGCAACAGCTACAGGTGTGCATTCCCAGCYTGTGCTGACTCAA
```

```
-SLIC-huVl5-for (SEQ ID NO: 39):
TAGCAACAGCTACAGGTGTGCATTCCCAGSCTGTGCTGACTCAG -SLIC-huVl6-for (SEQ ID NO: 40):
TAGCAACAGCTACAGGTGTGCATTCCAATTTTATGCTGACTCAG -SLIC-huVl7-for (SEQ ID NO: 41):
TAGCAACAGCTACAGGTGTGCATTCCCAGRCTGTGGTGACTCAG -SLIC-huVl8-for (SEQ ID NO: 42):
TAGCAACAGCTACAGGTGTGCATTCCCAGACTGTGGTGACCCAG -SLIC-huVl9-for (SEQ ID NO: 43):
TAGCAACAGCTACAGGTGTGCATTCCCWGCCTGTGCTGACTCAG -SLIC-huVlambda10-for (SEQ ID NO: 44):
TAGCAACAGCTACAGGTGTGCATTCCCAGGCAGGGCTGACTCAG -huCl-1-rev (SEQ ID NO: 45):
TCTCCACGGTGCTCCCTTC
```

Primer For Amplification of Human Immunoglobulin Expression Plasmid

Amplification of Heavy Chain Expression Plasmid Backbone:

```
-huIg-PCR-vectorprimer-as (SEQ ID NO: 46):
GGAATGCACACCTGTAGCTGTTGCTA

-huIg-PCR-vectorprimer-VH-s (SEQ ID NO: 47):
AAGCCCAGCAACACCAAGGTGGAC
```

Amplification of Kappa Light Chain Expression Plasmid Backbone:

```
-huIg-PCR-vectorprimer-as kappa (SEQ ID NO: 48):
GGAATGCACACCTGTAGCTGTTGCTA

-huIg-PCR-vectorprimer-VK-s (SEQ ID NO: 49):
GAGCTTCAACAGGGGAGAGTGT
```

Amplification of Lambda Light Chain Expression Plasmid Backbone:

```
-huIg-PCR-vectorprimer-as lambda (SEQ ID NO: 50):
GGAATGCACACCTGTAGCTGTTGCTA -huIg-PCR-vectorprimer-VL-s (SEQ ID NO: 51):
GAAGGGAGCACCGTGGAGA
```

Example 4

Pool Compared to Single Clones

Antibody variable region gene segments were amplified and cloned into the respective expression vectors as described in Example 1. To determine the fidelity of sequences derived from pool-cloning versus conventional clone-picking from single colonies, the transformation mix was split in two halves; one half was plated conventionally to generate single colonies while the other half was grown directly as pool-culture. Subsequently, plasmid was prepared both the pool-transformed E. coli cells as well as from single colonies picked from the conventional plates and the sequences of the cloned variable region gene segments was determined. As shown in the following Table 3, between 80% and 100% of colony-derived plasmids contained a correct variable region gene segment which was identical to the sequence obtained from the pool-transformation.

TABLE 3

| B-cell Clone No. | Number of most abundant LC sequence/total number of sequences | Number of most abundant HC sequence/total number of sequences |
|---|---|---|
| 5 | 10/11 | 8/12 |
| 6 | 11/12 | 12/12 |
| 10 | 2/2 | 8/12 |
| 35 | 6/6 | 7/12 |
| 38 | 11/12 | 12/12 |
| 39 | 9/11 | 10/12 |
| 42 | 3/5 | 11/12 |
| 50 | 6/6 | 6/7 |

The VH and VL encoding nucleic acid sequence obtained from the sequencing of the pool cultivated cells were identical to the most abundant sequence obtained from the sequencing of individual clones.

What is claimed is:

1. A method for producing an antibody, the method comprising: recovering the antibody from the cultivation medium of a eukaryotic cell, wherein the eukaryotic cell comprises nucleic acid encoding the antibody, whereby the nucleic acid encoding the antibody is obtained by
   (a) co-cultivating individual mature rabbit B-cells with feeder cells in individual containers;
   (b) determining the expression yield of the rabbit B-cells in 7 days of co-cultivation with feeder cells;
   (c) selecting those rabbit B-cells that produce more than 20 ng/ml antibody in 7 days of co-cultivation with feeder cells;
   (d) amplifying from the selected rabbit B-cells producing more than 20 ng/ml antibody in 7 days of co-cultivation with feeder cells the nucleic acid encoding the antibody light chain variable domain or the antibody heavy chain variable domain by PCR using single-stranded cDNA obtained from the RNA of the antibody-secreting rabbit B-cells as template, thereby obtaining a pool of nucleic acids encoding the antibody light chain variable domain or and the antibody heavy chain variable domain;
   (e) inserting the amplified pool of nucleic acids encoding the antibody light chain variable domain or and the antibody heavy chain variable domain into a eukaryotic expression plasmid by ligation-independent cloning; and
   (f) culturing a eukaryotic cell comprising the eukaryotic expression plasmid produced in (f) in cultivation media and recovering the antibody therefrom.

2. The method of claim 1, wherein PCR primers comprising the nucleic acid sequences of SEQ ID NOs: 5 and 6 or the nucleic acid sequences of SEQ ID NOs: 7 or 8 are used for the amplification of nucleic acid encoding the antibody light chain variable domain or the antibody heavy chain variable domain, respectively.

3. The method of claim 1, wherein method further comprises removing PCR primers after the PCR amplification step.

4. The method of claim 1, wherein the inserting of the amplified nucleic acids encoding the antibody light chain variable domain or the antibody heavy chain variable domain into a eukaryotic expression plasmid is by sequence and ligation-independent cloning.

5. The method of claim 1, wherein about 300 ng nucleic acid is used in the insertion step.

6. The method of claim 4, wherein the plasmid is linearized prior to amplification.

* * * * *

SEQUENCE LISTING

```
<160> NUMBER OF SEQ ID NOS: 51

<210> SEQ ID NO 1
<211> LENGTH: 2
<212> TYPE: PRT
<213> ORGANISM: Artificial Sequence
<220> FEATURE:
<223> OTHER INFORMATION: linker peptide 1

<400> SEQUENCE: 1

Gly Ser
1

<210> SEQ ID NO 2
<211> LENGTH: 3
<212> TYPE: PRT
<213> ORGANISM: Artificial Sequence
<220> FEATURE:
<223> OTHER INFORMATION: linker peptide 2

<400> SEQUENCE: 2

Gly Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: linker peptide 3

<400> SEQUENCE: 3

Gly Gly Gly Ser
1

<210> SEQ ID NO 4
<211> LENGTH: 5
<212> TYPE: PRT
<213> ORGANISM: Artificial Sequence
<220> FEATURE:
<223> OTHER INFORMATION: linker pepetide 4

<400> SEQUENCE: 4

Gly Gly Gly Gly Ser
1               5

<210> SEQ ID NO 5
<211> LENGTH: 37
<212> TYPE: DNA
<213> ORGANISM: Artificial Sequence
<220> FEATURE:
<223> OTHER INFORMATION: HC isolation primer
```

```
<400> SEQUENCE: 5
aagcttgcca ccatggagac tgggctgcgc tggcttc                             37

<210> SEQ ID NO 6
<211> LENGTH: 21
<212> TYPE: DNA
<213> ORGANISM: Artificial Sequence
<220> FEATURE:
<223> OTHER INFORMATION: HC isolation primer 2

<400> SEQUENCE: 6
ccattggtga gggtgcccga g                                              21

<210> SEQ ID NO 7
<211> LENGTH: 34
<212> TYPE: DNA
<213> ORGANISM: Artificial Sequence
<220> FEATURE:
<223> OTHER INFORMATION: LC isolation primer 1

<400> SEQUENCE: 7
aagcttgcca ccatggacay gagggccccc actc                                34

<210> SEQ ID NO 8
<211> LENGTH: 26
<212> TYPE: DNA
<213> ORGANISM: Artificial Sequence
<220> FEATURE:
<223> OTHER INFORMATION: LC isolation primer 2

<400> SEQUENCE: 8
cagagtrctg ctgaggttgt aggtac                                         26

<210> SEQ ID NO 9
<211> LENGTH: 26
<212> TYPE: DNA
<213> ORGANISM: Artificial Sequence
<220> FEATURE:
<223> OTHER INFORMATION: LC plasmid amplification primer 1

<400> SEQUENCE: 9
gtacctacaa cctcagcagc actctg                                         26

<210> SEQ ID NO 10
<211> LENGTH: 43
<212> TYPE: DNA
<213> ORGANISM: Artificial Sequence
<220> FEATURE:
<223> OTHER INFORMATION: LC plasmid amplification primer 2

<400> SEQUENCE: 10
ccctcrtgtc catggtggca agcttcctct gtgttcagtg ctg                      43

<210> SEQ ID NO 11
<211> LENGTH: 27
<212> TYPE: DNA
<213> ORGANISM: Artificial Sequence
<220> FEATURE:
<223> OTHER INFORMATION: HC plasmid amplification primer 1

<400> SEQUENCE: 11
tgggaactcg ggcaccctca ccaatgg                                        27

<210> SEQ ID NO 12
<211> LENGTH: 43
```

<212> TYPE: DNA
<213> ORGANISM: Artificial Sequence
<220> FEATURE:
<223> OTHER INFORMATION: HC plasmid amplification primer 2

<400> SEQUENCE: 12
gcccagtctc catggtggca agcttcctct gtgttcagtg ctg            43

<210> SEQ ID NO 13
<211> LENGTH: 32
<212> TYPE: DNA
<213> ORGANISM: Artificial Sequence
<220> FEATURE:
<223> OTHER INFORMATION: rb-V-kappa-HindIIIs primer

<400> SEQUENCE: 13
gattaagctt atggacayga gggcccccac tc                         32

<210> SEQ ID NO 14
<211> LENGTH: 35
<212> TYPE: DNA
<213> ORGANISM: Artificial Sequence
<220> FEATURE:
<223> OTHER INFORMATION: rb-C-kappa-NheIas primer

<400> SEQUENCE: 14
gatcgctagc cctggcaggc gtctcrctct aacag                      35

<210> SEQ ID NO 15
<211> LENGTH: 23
<212> TYPE: DNA
<213> ORGANISM: Artificial Sequence
<220> FEATURE:
<223> OTHER INFORMATION: rb-CH1rev-1 primer

<400> SEQUENCE: 15 gcaggggggcc agtgggaaga ctg                                  23

<210> SEQ ID NO 16
<211> LENGTH: 29
<212> TYPE: DNA
<213> ORGANISM: Artificial Sequence
<220> FEATURE:
<223> OTHER INFORMATION: rbVH3-23for3 primer

<400> SEQUENCE: 16
caccatggag actgggctgc gctggcttc                             29

<210> SEQ ID NO 17
<211> LENGTH: 20
<212> TYPE: DNA
<213> ORGANISM: Artificial Sequence
<220> FEATURE:
<223> OTHER INFORMATION: bcPCR-huCgamma-rev primer

<400> SEQUENCE: 17
cccccagagg tgctcttgga                                       20

<210> SEQ ID NO 18
<211> LENGTH: 20
<212> TYPE: DNA
<213> ORGANISM: Artificial Sequence
<220> FEATURE:
<223> OTHER INFORMATION: bcPCR-FHLC-leader-fw primer

<400> SEQUENCE: 18
atggacatga gggtccccgc                                          20

<210> SEQ ID NO 19
<211> LENGTH: 24
<212> TYPE: DNA
<213> ORGANISM: Artificial Sequence
<220> FEATURE:
<223> OTHER INFORMATION: bcPCR-huCkappa-rev primer

<400> SEQUENCE: 19
gatttcaact gctcatcaga tggc                                      24

<210> SEQ ID NO 20
<211> LENGTH: 45
<212> TYPE: DNA
<213> ORGANISM: Artificial Sequence
<220> FEATURE:
<223> OTHER INFORMATION: bcPCR-hu-HC-10600-SLIC-as primer

<400> SEQUENCE: 20
cagcccagtc tccatggtgg caagcttcct ctgtgttcag tgctg               45

<210> SEQ ID NO 21
<211> LENGTH: 26
<212> TYPE: DNA
<213> ORGANISM: Artificial Sequence
<220> FEATURE:
<223> OTHER INFORMATION: bcPCR-hu-HC-10600-SLIC-s  primer

<400> SEQUENCE: 21
ctccaagagc acctctgggg gcacag                                    26

<210> SEQ ID NO 22
<211> LENGTH: 24
<212> TYPE: DNA
<213> ORGANISM: Artificial Sequence
<220> FEATURE:
<223> OTHER INFORMATION: bcPCR-hu-LC-10603-SLIC-s  primer

<400> SEQUENCE: 22
gccatctgat gagcagttga aatc                                      24

<210> SEQ ID NO 23
<211> LENGTH: 38
<212> TYPE: DNA
<213> ORGANISM: Artificial Sequence
<220> FEATURE:
<223> OTHER INFORMATION: bcPCR-hu-LC-10603-SLIC-as  primer

<400> SEQUENCE: 23
gcggggaccc tcatgtccat ggtggcaagc ttcctctg                       38

<210> SEQ ID NO 24
<211> LENGTH: 48
<212> TYPE: DNA
<213> ORGANISM: Artificial Sequence
<220> FEATURE:
<223> OTHER INFORMATION: SLIC-hu-VHuniversal-for  primer

<400> SEQUENCE: 24
agcaacagct acaggtgtgc attccgaggt gcagctgktg sagtctgs            48

<210> SEQ ID NO 25
<211> LENGTH: 45
<212> TYPE: DNA
<213> ORGANISM: Artificial Sequence -continued

```
<220> FEATURE:
<223> OTHER INFORMATION: SLIC-hu-VH6-for primer

<400> SEQUENCE: 25
agcaacagct acaggtgtgc attcccaggt rcagctgcag sagtc            45

<210> SEQ ID NO 26
<211> LENGTH: 24
<212> TYPE: DNA
<213> ORGANISM: Artificial Sequence
<220> FEATURE:
<223> OTHER INFORMATION: hu-CH1gamma-rev primer

<400> SEQUENCE: 26
gtccaccttg gtgttgctgg gctt                                   24

<210> SEQ ID NO 27
<211> LENGTH: 47
<212> TYPE: DNA
<213> ORGANISM: Artificial Sequence
<220> FEATURE:
<223> OTHER INFORMATION: SLIC-huVk2-for primer

<400> SEQUENCE: 27
tagcaacagc tacaggtgtg cattccgatg ttgtgatgac tcagtct          47

<210> SEQ ID NO 28
<211> LENGTH: 47
<212> TYPE: DNA
<213> ORGANISM: Artificial Sequence
<220> FEATURE:
<223> OTHER INFORMATION: SLIC-huVk3-for primer

<400> SEQUENCE: 28
tagcaacagc tacaggtgtg cattccgaaa ttgtgwtgac rcagtct          47

<210> SEQ ID NO 29
<211> LENGTH: 44
<212> TYPE: DNA
<213> ORGANISM: Artificial Sequence
<220> FEATURE:
<223> OTHER INFORMATION: SLIC-huVk5-for primer

<400> SEQUENCE: 29
tagcaacagc tacaggtgtg cattccgaca tcgtgatgac ccag             44

<210> SEQ ID NO 30
<211> LENGTH: 47
<212> TYPE: DNA
<213> ORGANISM: Artificial Sequence
<220> FEATURE:
<223> OTHER INFORMATION: SLIC-huVk7-for primer

<400> SEQUENCE: 30
tagcaacagc tacaggtgtg cattccgaaa ttgtgctgac tcagtct          47

<210> SEQ ID NO 31
<211> LENGTH: 49
<212> TYPE: DNA
<213> ORGANISM: Artificial Sequence
<220> FEATURE:
<223> OTHER INFORMATION: SLIC-huVk8-for primer

<400> SEQUENCE: 31
tagcaacagc tacaggtgtg cattccgawr ttgtgmtgac kcagtctcc        49
```

```
<210> SEQ ID NO 32
<211> LENGTH: 47
<212> TYPE: DNA
<213> ORGANISM: Artificial Sequence
<220> FEATURE:
<223> OTHER INFORMATION: SLIC-huVk1long-for primer

<400> SEQUENCE: 32
tagcaacagc tacaggtgtg cattccgaca tccrgwtgac ccagtct         47

<210> SEQ ID NO 33
<211> LENGTH: 47
<212> TYPE: DNA
<213> ORGANISM: Artificial Sequence
<220> FEATURE:
<223> OTHER INFORMATION: SLIC-huVk2longw-for primer

<400> SEQUENCE: 33
tagcaacagc tacaggtgtg cattccgatr ttgtgatgac ycagwct         47

<210> SEQ ID NO 34
<211> LENGTH: 22
<212> TYPE: DNA
<213> ORGANISM: Artificial Sequence
<220> FEATURE:
<223> OTHER INFORMATION: huCk-rev primer

<400> SEQUENCE: 34
acactctccc ctgttgaagc tc                                     22

<210> SEQ ID NO 35
<211> LENGTH: 44
<212> TYPE: DNA
<213> ORGANISM: Artificial Sequence
<220> FEATURE:
<223> OTHER INFORMATION: SLIC-huVl1-for primer

<400> SEQUENCE: 35
tagcaacagc tacaggtgtg cattcccagt ctgtgytgac kcag             44

<210> SEQ ID NO 36
<211> LENGTH: 44
<212> TYPE: DNA
<213> ORGANISM: Artificial Sequence
<220> FEATURE:
<223> OTHER INFORMATION: SLIC-huVl2-for primer

<400> SEQUENCE: 36
tagcaacagc tacaggtgtg cattcccagt ctgccctgac tcag             44

<210> SEQ ID NO 37
<211> LENGTH: 44
<212> TYPE: DNA
<213> ORGANISM: Artificial Sequence
<220> FEATURE:
<223> OTHER INFORMATION: SLIC-huVl3-for primer

<400> SEQUENCE: 37
tagcaacagc tacaggtgtg cattcctcct atgagctgay wcag             44

<210> SEQ ID NO 38
<211> LENGTH: 44
<212> TYPE: DNA
<213> ORGANISM: Artificial Sequence
<220> FEATURE:
<223> OTHER INFORMATION: SLIC-huVl4-for primer
```

<400> SEQUENCE: 38
tagcaacagc tacaggtgtg cattcccagc ytgtgctgac tcaa                44

<210> SEQ ID NO 39
<211> LENGTH: 44
<212> TYPE: DNA
<213> ORGANISM: Artificial Sequence
<220> FEATURE:
<223> OTHER INFORMATION: SLIC-huVl5-for primer

<400> SEQUENCE: 39
tagcaacagc tacaggtgtg cattcccags ctgtgctgac tcag                44

<210> SEQ ID NO 40
<211> LENGTH: 44
<212> TYPE: DNA
<213> ORGANISM: Artificial Sequence
<220> FEATURE:
<223> OTHER INFORMATION: SLIC-huVl6-for primer

<400> SEQUENCE: 40
tagcaacagc tacaggtgtg cattccaatt ttatgctgac tcag                44

<210> SEQ ID NO 41
<211> LENGTH: 44
<212> TYPE: DNA
<213> ORGANISM: Artificial Sequence
<220> FEATURE:
<223> OTHER INFORMATION: SLIC-huVl7-for primer

<400> SEQUENCE: 41
tagcaacagc tacaggtgtg cattcccagr ctgtggtgac tcag                44

<210> SEQ ID NO 42
<211> LENGTH: 44
<212> TYPE: DNA
<213> ORGANISM: Artificial Sequence
<220> FEATURE:
<223> OTHER INFORMATION: SLIC-huVl8-for primer

<400> SEQUENCE: 42
tagcaacagc tacaggtgtg cattcccaga ctgtggtgac ccag                44

<210> SEQ ID NO 43
<211> LENGTH: 44
<212> TYPE: DNA
<213> ORGANISM: Artificial Sequence
<220> FEATURE:
<223> OTHER INFORMATION: SLIC-huVl9-for primer

<400> SEQUENCE: 43
tagcaacagc tacaggtgtg cattcccwgc ctgtgctgac tcag                44

<210> SEQ ID NO 44
<211> LENGTH: 44
<212> TYPE: DNA
<213> ORGANISM: Artificial Sequence
<220> FEATURE:
<223> OTHER INFORMATION: SLIC-huVlambda10-for primer

<400> SEQUENCE: 44
tagcaacagc tacaggtgtg cattcccagg cagggctgac tcag                44

<210> SEQ ID NO 45

```
<211> LENGTH: 19
<212> TYPE: DNA
<213> ORGANISM: Artificial Sequence
<220> FEATURE:
<223> OTHER INFORMATION: huCl-1-rev  primer

<400> SEQUENCE: 45
tctccacggt gctcccttc                                              19

<210> SEQ ID NO 46
<211> LENGTH: 26
<212> TYPE: DNA
<213> ORGANISM: Artificial Sequence
<220> FEATURE:
<223> OTHER INFORMATION: huIg-PCR-vectorprimer-as

<400> SEQUENCE: 46
ggaatgcaca cctgtagctg ttgcta                                      26

<210> SEQ ID NO 47
<211> LENGTH: 24
<212> TYPE: DNA
<213> ORGANISM: Artificial Sequence
<220> FEATURE:
<223> OTHER INFORMATION: huIg-PCR-vectorprimer-VH-s

<400> SEQUENCE: 47
aagcccagca acaccaaggt ggac                                        24

<210> SEQ ID NO 48
<211> LENGTH: 26
<212> TYPE: DNA
<213> ORGANISM: Artificial Sequence
<220> FEATURE:
<223> OTHER INFORMATION: huIg-PCR-vectorprimer-as kappa

<400> SEQUENCE: 48
ggaatgcaca cctgtagctg ttgcta                                      26

<210> SEQ ID NO 49
<211> LENGTH: 22
<212> TYPE: DNA
<213> ORGANISM: Artificial Sequence
<220> FEATURE:
<223> OTHER INFORMATION: huIg-PCR-vectorprimer-VK-s

<400> SEQUENCE: 49
gagcttcaac aggggagagt gt                                          22

<210> SEQ ID NO 50
<211> LENGTH: 26
<212> TYPE: DNA
<213> ORGANISM: Artificial Sequence
<220> FEATURE:
<223> OTHER INFORMATION: huIg-PCR-vectorprimer-as lambda

<400> SEQUENCE: 50
ggaatgcaca cctgtagctg ttgcta                                      26

<210> SEQ ID NO 51
<211> LENGTH: 19
<212> TYPE: DNA
```

```
<213> ORGANISM: Artificial Sequence
<220> FEATURE:
<223> OTHER INFORMATION: huIg-PCR-vectorprimer-VL-s

<400> SEQUENCE: 51
gaagggagca ccgtggaga                                                  19
```